(12) United States Patent
Drahos et al.

(10) Patent No.: US 6,824,772 B2
(45) Date of Patent: Nov. 30, 2004

(54) BACILLUS LICHENIFORMIS BIOFUNGICIDE

(75) Inventors: David J. Drahos, Roanoke, VA (US); Lee West, Catawba, VA (US)

(73) Assignee: Novozymes Biologicals, Inc.

( * ) Notice: Subject to any disclaimer, the term of this patent is extended or adjusted under 35 U.S.C. 154(b) by 185 days.

(21) Appl. No.: 10/043,297

(22) Filed: Jan. 14, 2002

(65) Prior Publication Data

US 2003/0082165 A1 May 1, 2003

Related U.S. Application Data

(63) Continuation-in-part of application No. 09/887,379, filed on Jun. 22, 2001, now Pat. No. 6,569,425.

(51) Int. Cl.[7] .................................................. A01N 63/00
(52) U.S. Cl. .................. 424/93.46; 435/93.3; 435/93.1; 435/253.6; 435/170; 435/244; 435/171
(58) Field of Search .............................. 424/93.46, 93.1, 424/93.3; 435/253.6, 170, 244, 171

(56) References Cited

U.S. PATENT DOCUMENTS

| 4,878,936 A | * | 11/1989 | Handelsman et al. ............ 71/7 |
| 5,614,188 A | * | 3/1997 | Urano et al. .............. 424/93.46 |

* cited by examiner

*Primary Examiner*—Irene Marx
(74) *Attorney, Agent, or Firm*—Mishrilal Jain

(57) ABSTRACT

The invention discloses an isolated, biologically pure culture of a microorganism, *Bacillus licheniformis*, strain SB3086 for use as an environmentally desirable biofungicide. The invention also discloses a method for enhancing biofungicidal activity of a microbial agent. The inventional further discloses a nutrient composition comprising a microbial agent and a method for controlling plant fungal diseases and infestation of *Aspergillis niger* utilizing, said strain.

1 Claim, 2 Drawing Sheets

Fig. 1. Reduction of *Sclerotinia homoeocarpa* (Dollar Spot) disease by *B. licheniformis* SB3086
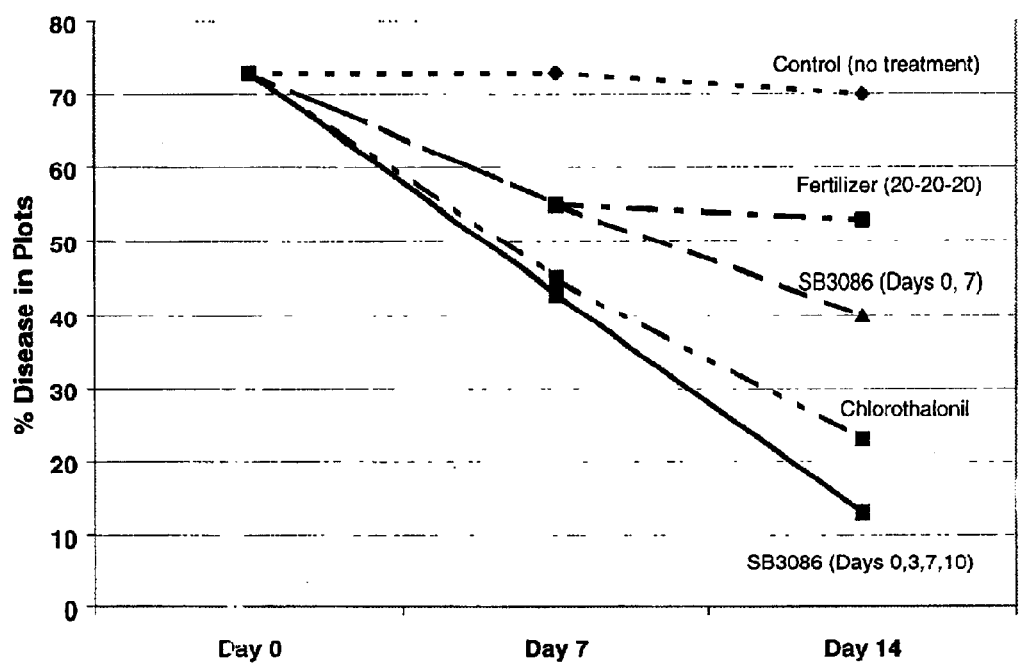

Fig. 2. Disease control in the field.
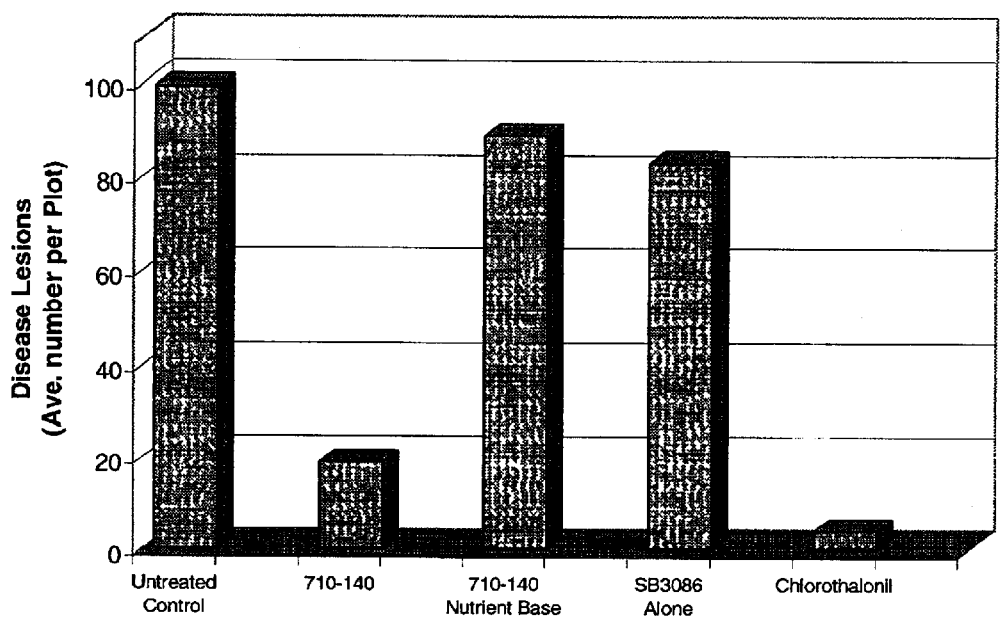

*BACILLUS LICHENIFORMIS* BIOFUNGICIDE

This a continuation in part of a presently application Ser. No. 09/887,379 filed Jun. 22, 2001 now U.S. Pat. No. 6,569,425.

FIELD OF THE INVENTION

The present invention relates to a biofungicide. In particular, the present invention relates to a microorganism, *Bacillus licheniformis* strain SB3086, which controls the growth of fungal organisms, including plant diseases caused by fungi, and a composition comprising said strain SB3086.

BACKGROUND OF THE INVENTION

Diseases caused by fungal species are considered among the most widespread and damaging of plants worldwide. Presently, control of plant fungal diseases is largely dependent upon the application of certain chemicals. Although some of these chemicals are known to have negative environmental and human health problems, nevertheless such chemical agents continue to be in wide use due to their strong activity against important fungal diseases, and availability of environmentally safer and effective alternatives.

Generally, biological control of diseases commonly infecting plants in the root zone (rhizosphere) and the leaf zone (phylloplane) are preferred over more traditional synthetic chemical control methodologies. Such biocontrol agents usually cause little or no injury to the plant host or the environment, and some may even favor normal plant development. However, most such biocontrol organisms are typically very limited either in the scope of their effectiveness against fungal diseases, or in their ability to survive under practical field conditions and during treatment applications.

Attempts have been made to control plant fungal diseases by using certain microorganisms. For example, U.S. Pat. No. 5,589,381 (Neyra and Sadasivan, 1996) describes a *Bacillus licheniformis* strain PR1-36a with some ability to inhibit certain plant pathogens. However, efforts to apply certain live biological control organisms have been greatly limited by the narrow range of their effectiveness against plant pathogens, or by the inherent instability of these organisms. Many strains often succumb within weeks to standard storage conditions, or within hours to typical field conditions involving relatively high temperatures, desiccation after spraying, and harmful effects of ultraviolet sunlight (UV) on the actively growing organism. Attempts to culture such organisms on-site at the location where the biocontrol strain would be applied have found some utility. However, serious difficulties with culture contamination, and the necessity for evening application to avoid temperature and UV effects often prove difficult, labor intensive, expensive, and impractical. Therefore, an environmentally safe and effective biological control method of inhibiting damage to plants caused by fungal diseases has heretofore not been achieved and it remains a long felt need in the agricultural industry over currently used hazardous chemicals.

SUMMARY OF THE INVENTION

It is, therefore, an object of the present invention to provide an environmentally favorable and effective biological agent for the control of a broad range of plant fungal diseases and other fungal organisms.

It is a further object of the present invention to provide a formulation and a biological method for controlling plant fungal diseases utilizing a unique strain of *Bacillus licheniformis* SB3086. The use of this strain SB3086 provides a practical, naturally occurring alternative to standard xenobiotic chemical agents, thereby providing an environmentally safer means to achieve fungal disease control or elimination in plants.

It is an additional object of the present invention to provide a composition containing said SB3086 strain in a form suitable for application to plants. Such a composition includes non-toxic surfactants, non-toxic amounts of plant nutrients, preservatives, biosupplements and the like, and may be in the form of active vegetative spores, liquid, flowable powder, granules, spray dried material or with another carrier material.

Another object of the present invention is to provide a method for controlling plant fungal diseases utilizing the biofungicide of the present invention. The biofungicide may be applied to the shoot, the root, the seeds, vegetative propagules or as a soil or plant treatment in any suitable form, such as a liquid, a spray, a powder, root dip, a granule, a dust and the like containing active vegetative cells.

A further object of the present invention is to provide a method for enhancing biofungicidal activity of a microbial agent, comprising applying a microorganism capable of producing a fungicidal agent, with a nutrient formulation that enhances biofungicidal activity of said microorganism.

Various other objects and advantages of the present invention will become evident from the following brief description of drawings and from the detailed description of the invention.

BRIEF DESCRIPTION OF DRAWINGS

In the drawings,

FIG. 1 shows the results of a study comparing various agents for controlling *Sclerotinia homoeocarpa* (Dollar Spot) disease including *Bacillus licheniformis* SB3086.

FIG. 2 shows the ability of the *B. licheniformis* SB3086 strain in the preferred 710-140 formulation to control Dollar Spot disease (*Sclerotinia homoeocarpa*) in a field trial on naturally infested turf.

DETAILED DESCRIPTION OF INVENTION

The above and various other objects and advantages of the present invention are achieved by a biologically pure culture of *Bacillus licheniformis* strain SB3086 having identifying characteristics of ATCC Deposit No.55406, and a composition that enhances biofungicidal activity of a microbial agent.

An important aspect of the present invention is to control plant pathogenic fungal species using biological organisms which function by natural antagonism or growth inhibition of the disease-causing fungi, thereby limiting the damage and spread of the harmful diseases. The invention in particular relates to the discovery of a novel bacterial soil isolate, *Bacillus licheniformis* SB3086, which unexpectedly possesses not only an unusually strong ability to produce potent inhibitory effect against a broad spectrum of fungal diseases, but also a natural ability to survive long-term storage and practical field application procedures or conditions.

It was discovered that *Bacillus licheniformis* SB3086 has an unusual and surprising property of forming a dense spore coat with a high relative resistance to damage by Ultraviolet light from the sun (UV). It was also found to be resistant to loss of viability due to desiccation and high temperature often encountered under field conditions. Furthermore, the invention has achieved a practical, large-scale industrial growth of excellent quality SB3086 spores in a highly concentrated liquid form ranging from about $10^4$ to about $10^{12}$ CFU/ml The concentrated spores could also be spray dried and used as a flowable powder with concentrations ranging from about $10^5$ to about $10^{13}$ CFU/gram or in some other suitable form.

It should be understood that unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the methods and materials described herein are preferred. Unless mentioned otherwise, the techniques employed or contemplated herein are standard methodologies well known to one of ordinary skill in the art. The materials, methods and examples are only exemplary and not limiting.

The term "biocontrol" or "biofungicide" as used herein means controlling or eliminating the fungal activity by biological means, such as by using a bacterium, as opposed to the use of a synthetic chemical agent.

The term "enhancing biofungicidal activity" as used herein means that the biofungicidal activity of a microbial agent is significantly or substantially greater when applied in association or combination with the nutrient formulation than that obtained without the use of the nutrient formulation.

The term "biosupplement" as used herein is defined as those naturally-occurring materials recognized to be of direct or indirect benefit to plant growth, hardiness, yield, or quality, other than commonly recognized inorganic nutrients and micronutrients. Examples of such biosupplements include: i) sea plant extracts, such as that obtained from the Norwegian kelp plant *Ascophyllum nodosum*; ii) animal manures and processed sewage sludge; iii) animal-derived products, such as bone, feather, hair, and fish meal; iv) humic and fulvic acid materials, such as from mined leornardite, peat ;v) paper processing by-products (e.g. lignin sulfonate); vi) compost material obtained by microbial metabolism and partial degradation of plant and animal waste substances; and the like.

The term "Propagule" as used herein refers to a component or a section of a plant containing all the essential elements to enable regrowth into a full plant and/or propagation of desired plant components. Example of such propagules include: i) seeds; ii) eyes or "seedpieces", such as from potatoes; iii) stem cuttings which may be placed under suitable growth conditions to form new roots; iv) root or rhizome section; and the like.

The natural soil microorganism, *Bacillus licheniformis* SB3086, has been found to be effective against a broad array of important plant pathogenic fungi, including *Sclerotinia homoeocarpa* (Dollar Spot disease), *Rhizoctonia solani* (*Rhizoctonia* blight), *Rhizoctonia oryzae* (*Rhizoctonia* Sheath Spot), *Pyricularia grisea* (Gray Leaf Spot), *Microdochium nivale* (Pink Snow Mold), and *Bipolaris unique organism, practitioners in the industry can now employ biological control methods against fungal infestation. Unique attributes of SB*3086 include: efficient and rapid growth under standard large-scale fermentation conditions and media; broad temperate range for optimal growth (18° C.–50° C.); propensity to form stable spores in a high percentage of vegetative bacterial population under known fermentation procedures; ability of the spores to survive for long periods under sub-optimal conditions, such as extremes of temperature and desiccation; inherent resistance of the spores to UV sunlight; ability to grow under low oxygen conditions typically encountered in the soil and root environment; capacity to colonize the root and leaf surface of plants; and its verified safety to animals and plants based on standard toxicology and pathogenicity studies.

Taxonomic characteristics of *Bacillus licheniformis* SB3086 compared with standard characteristics of *Bacillus licheniformis* and *Bacillus subtilis* species are listed in Table 1.

*Bacillus licheniformis* SB3086 has been deposited with the American Type Culture Collection, 10801 University Blvd., Manassas, Va. 20110, U.S.A., under accession number ATCC 55406. The deposit shall be maintained in viable condition at the ATCC during the entire term of the issued patent and shall be made available to any person or entity for non-commercial use without restriction, but in accordance with the provisions of the law governing the deposit.

Various embodiments of the invention are now described.

EXAMPLE 1

Isolation of *Bacillus licheniformis* SB3086

Soil samples and root wash material were gathered from healthy plant and turf roots and adjacent areas. Individual isolates were obtained by dilution plate analysis on a variety of solid growth media in such a way as to select for bacterial strains capable of spore-formation. Specifically, roots of vegetable and turfgrass plants were washed in a sterile phosphate buffer, then heated at 80° C. for 10 minutes. The heat-shocked washing was subsequently diluted in fresh buffer at 10-fold increments, and spread onto Standard Methods agar plates and incubated overnight at 32° C. Individual colonies were separately cultured and screened for the ability to inhibit the indicator fungus Geotrichum, as well as certain other plant-pathogenic fungi. Those able to inhibit this indicator fungus, were selected for further comparative testing against additional plant pathogenic fungal species. To assess anti-fungal activity on indicator plates, a small circular plug (4 mm) of the target fungus (taken from a culture growing on semi-solid medium) was placed in the center of a sterile 15 cm petri plate containing commercially available Potato Dextrose Agar. At the same time, 5 $\mu$l volumes of individual overnight cultures of the candidate bacterial isolates to be tested (grown in LB broth) were separately placed approximately 3 cm from the fungal plug. Evidence of inhibition were recorded after 3–4 days incubation at 23° C.

EXAMPLE 2

Performance Comparison of *Bacillus licheniformis* SB3086 with other *Bacillus licheniformis* Type Strains While *B. licheniformis* SB3086 shares features in common with other known *B. licheniformis* strains available from public sources (e.g., ATCC), it is uniquely different at least in its unexpectedly strong ability to inhibit the growth of a wide variety of plant pathogenic fungi. This surprising attribute was determined as follows.

As described in Example 1, small circular plugs were taken from actively growing cultures of the plant fungal disease pathogens: *Sclerotinia homoeocarpa* (Dollar Spot); *Rhizoctonia solani* (*Rhizoctonia* blight), *Rhizoctonia oryzae* (*Rhizoctonia* Sheath Spot), *Pyricularia grisea* (Gray Leaf Spot), *Microdochium nivale* (Pink Snow, Mold), and *Drechslera dictyoides* (*Helminthosporium* blight). These circular plugs were placed in the center of a petri dish containing a standard growth medium (such as Potato Dextose Agar), inhibition of the outgrowth of these fungi by four different *Bacillus licheniformis* strains were assessed, and rated (as noted in Example 1) on a graduated scale with 5=strong inhibition to 0=no inhibition. The results are presented in Table 2. These results clearly demonstrate superior performance of *B. licheniformis* SB3086 across a broad spectrum of plant disease types. This is particularly true on Dollar Spot (*Sclerotinia homoeocarpa*), where the prior art bacterial strain *B. licheniformis* PR1-36a (U.S. Pat. No. 5,589,381, Neyra and Sadasivan) performed very poorly relative to SB3086.

EXAMPLE 3

Performance Comparison of *Bacillus licheniformis* SB3086 with a Variety of other Soil Microbial Isolates The ability of a single soil microbe such as *B. licheniformis* SB3086 to display strong anti-fungal activity against a wide variety of target fungi is a surprising and uncommon feature of this soil bacteria as demonstrated by the results presented in Table 4, where distinct anti-fungal activity by a variety of microorganisms from several genus and species was compared with SB3086. Specifically, as criteria, two distinct fungal inhibition traits were examined. The first trait (A) is the darkening discoloration of the disease fungal mycelia at the interface with the advancing anti-fungal agents of the test bacterial colonies. This darkening is often associated with increased production of melanin by the fungus, believed to be a part of the fungal defense mechanism. The second trait (B) assesses the capability of the biocontrol bacteria to inhibit the growth and advance of the fungal hyphae. This is indicated by a clear inhibition zone between the growing bacterial colony and the advancing fungus.

While some strains exhibit certain anti-fungal characteristics in common with SB3086, most exhibit limited activities, and none were found to have as extensive or strong an activity as SB3086.

EXAMPLE 4

Ability of *B. licheniformis* SB3086 to Inhibit the Growth of other Non-desirable Fungi The anti-fungal ability of *B. licheniformis* SB3086 also extends to other undesirable fungal organisms for which control may be important in other situations. For example, SB3086 is capable of inhibiting the growth of *Aspergillis niger*, a common fungi causing darkening and discoloration of bathroom tile and grout. As shown in Table 4, SB3086 is superior in reducing the growth of this strain, compared with organisms known to be useful in odor reduction and other janitorial applications.

EXAMPLE 5

Field Performance of *Bacillus licheniformis* SB3086 for Control of Fungal Disease Having demonstrated the broad range antifungal efficacy of SB3086 by laboratory tests, studies were undertaken to demonstrate the function and hardiness of such a biocontrol microbe under actual field conditions. This field performance ability was demonstrated for *B. licheniformis* SB3086 on growing plants in their native habitat, under attack by a naturally-occurring fungal disease pathogen.

For this study, an economically important turf plant, Penncross Bentgrass, widely used in golf course and sport fields, was selected as a representative test subject. A fungal pathogen, *Sclerotinia homoeocarpa* (Dollar Spot disease), severely damages this turf grass ravaging the golf course and the sport fields. Results indicated that the infestation of *Sclerotinia homoeocarpa* was strongly inhibited on established turfgrass following spray applications of a spore suspension of SB3086. A concentrated spore formulation containing approximately $1.0 \times 10^9$ CFU/ml of SB3086 was applied at a rate of 18 oz./1000 sq. ft. as a foliar spray to established Penncross Bentgrass uniformly infested with Dollar Spot disease. The treatments were applied to four 2 ft.×4 ft. plots located randomly among similar infested turfgrass plots. Comparative replicated plots were treated with either fertilizer (Peter's 20-20-20 at 0.2 lbs. nitrogen/1000 sq. ft.), the chemical control agent chlorothalonil (Daconil WS at 8 oz./1000 sq. ft.), or water (control). Treatments were made as follows: SB3086 at Days 0 and 7; SB3086 at Days 0, 3, 7, and 10; Peter's® fertilizer at Days, 0 and 7; and chlorothalonil at Day 0 (as per manufacturer's recommendation). Assessments of disease infestation, based on the percent coverage of individual plots, were made Days 0, 7, and 14.

The results are presented in FIG. 1. It is clear from the data that the spray application of the spore suspension of SB3086 provided a strong reduction in disease symptoms on the plant surface within 2 weeks of treatment initiation. Notably, the disease symptoms were already very evident prior to treatment initiation. While over 70% of the control (non-treated) plots continued to show visible disease decay after 14 days, less than 15% of the plot area of plants treated with *B. licheniformis* SB3086 exhibited any visible disease symptoms during the same period. Only the application of chemical disease control agent chlorothalonil was able to approach the curative disease capability of SB3086. It should be noted, of course, that the use of SB3086 offers a far more environmentally safe approach for fungal disease treatment on plants compared to the commonly used chemical control method of using chlorothalonil, which is not only a Class II Carcinogen but also toxic to fish and aquatic life.

EXAMPLE 6

Field Control of *Rhizoctonia* blight disease (Brown Patch) by *B. licheniformis* SB3086

To further demonstrate the breadth of field capability of *B. licheniformis* SB3086 to control plant diseases, field trials were cared out at three different locations under varying field and climate conditions using SB33086 against *Rhizoctonia* blight disease on naturally infected plants. Typically, *Rhizoctonia* blight is caused by the fungus, *Rhizoctonia solani* and is a disease common to many plants, including turfgrass, wheat, corn, shrubs, trees, most vegetables and perennial ornamentals. For these trials, both Fescue and Bentgrass varieties of established turfgrass exhibiting significant symptoms of *Rhizoctonia* blight was treated in multiple (3) randomized 3 ft.×5 ft. plots with an SB3086 spore suspension, containing about $1.0 \times 10^9$ CFU/ml, applied at a rate of 18 oz./1000 sq. ft. as a foliar spray every 7 days. Similar plots in the test area were treated with one of the two chemical control agents Daconil® (chlorothalonil; Zeneca Professional Products) or Heritage® (azoxystrobin; Zeneca Professional Products) at recommended rates and intervals, or remained as untreated Control plots. The percent disease reduction of each treatment relative to the untreated control plots is presented in Table 5.

The data show significant disease control by *B. licheniformis* SB3086 against *Rhizoctonia* blight (Brown Patch), although the disease reduction levels did not reach the levels observed with the chemical agents. However, these trials clearly demonstrate the breadth of disease target efficacy of SB3086 in the field on several plant type, in diverse locations and climate conditions.

Of course, the biofungicide may be applied to the plants in any suitable form, such as a spray, a powder, a granule, a liquid and the like. A formulation containing the biofungicide of the present invention may also include such common components as a surfactant, non-toxic amounts of plant nutrients (e.g. fertlizers and micronutrients) and the like as may be suggested to one of ordinary skill in the art.

EXAMPLE 7

Composition of a Formulation

A composition in accordance with the present invention is a concentrated liquid formulation which includes non-toxic amounts of plant nutrients and micronutrients, such as organic nitrogen, chelated zinc, chelated iron, as well as natural organic growth enhancing agents, such as sea plant extract. Inclusion of these ingredients, in addition to the active ingredient *B. licheniformis* SB3086 in the formulation, may assist the plant in recovery from the damage and stress encountered during disease attack. A preferred formulation in accordance with the present invention is presented in Table 6. Of course, as it may be suggested to those skilled in the art, other levels and types of nutrients, organic materials and the like may be substituted or added in the formulation.

The concentrate is usually diluted in about 2 to 300 volumes of water and applied by foliar spray. On turfgrass, the application rate is usually 18 ounces of the preferred formulation in 2 gallons of water sprayed on 1000 sq. ft. of turf surface using suitable liquid spray equipment. Such equipment might include application though a standard irrigation system. The amount of the preferred formulation which is applied may vary from about 2 to about 36 oz/1000 sq. ft. depending on disease pressure and overall plant health. Alternatively, a dry formulation of the invention may be prepared by spray-drying the *B. licheniformis* SB3086 spores into a flowable powder. This may then be blended with dry nutrients, micronutrients, and organic growth agents. For application, the dry formulation containing the spray dried spores of SB3086 is suspended in water to the preferred spore concentration of about $8.0 \times 10^7$ CFU/ml. Two gallons of this suspension are then applied on 1000 sq. ft. of plant surface, as described. The concentration of suspended spores applied per unit area may vary from about $5 \times 10^7$ CFU/sq. ft. to about $1 \times 10^{11}$ CFU/sq.ft. depending on disease pressure and type.

Field Trial

Field studies have demonstrated that significant effectiveness of the *Bacillus licheniformis* SB3086 strain to control fungal disease is best achieved when used in combination with the preferred organic nutrient supplements described in Table 6 hereof. Application of this microbe alone, even in a concentrated form, or of the nutrient formulation without the SB3086 strain (designated as 710-140 Nutrient Base) were significantly less effective in providing a commercially desirable level of disease control. Without being bound to any theory or mechanism of action and the like, this phenomenon may be because the application of SB3086 in spore form, as is standard for a stable commercial product, requires plant exuded material to induce germination of the bacterial spores. Of course, only after germination into actively growing vegetative cells will the bacterial strains (e.g., SB3086 or the like) be able to produce the antifungal agent responsible for disease control. Carefully chosen nutrients in the formulation trigger the plant to produce and excrete substances such as key amino acids and sugars which in turn induce bacterial spore germination. This discovery may explain why many biofungicide agents which have some effectiveness under laboratory conditions are often incapable of demonstrating significant disease control under field conditions when applied without an effective nutrient formulation.

As demonstrated by the results shown in FIG. 2, the ability of the formulation of the present invention to reduce the average number of disease lesions is in the range of disease reduction obtained using a standard chemical fungicide (chlorothalonil). Treatments with the 710-140 Nutrient Base (without the SB3086 strain) or the SB3086 spores alone, were significantly less effective in controlling this disease under field conditions. In this field study, four replicates of 4 ft.×5 ft. randomized plots were treated twice per week as a foliar spray with the indicated material, except for plots receiving chlorothalonil (1.82 oz Daconil Ultrex® 82.5SDG), which was applied at the standard labeled rate and frequency. The preferred 710-140 formulation which included SB3086 and the 710-140 Nutrient Base (without the SB3086 strain) were applied at the rate of 20 oz./1000 sq. ft. The treatment with SB3086 alone (without the nutrient base) received at least the same number of spores per unit area as applied with the 710-140 preferred formulation.

The results shown in FIG. 2 clearly establish: (i) the significant efficacy of the SB3086 strain in a preferred nutrient formulation such as that in 710-140; and (ii) the much less effective performance of either the nutrient formulation without the SB3086 strain or the SB3086 strain itself when used apart from the preferred nutrient formulation.

Example embodiments have now been described in accordance with the objects and advantages of the present invention. It will be appreciated that these examples are merely illustrative and not limiting of the invention. Many variations and modifications will be apparent to those skilled in the art and all such variations and modifications are included within the purview and scope of the claims.

TABLE 1

Comparative Taxonomic Characteristics of *Bacillus licheniformis* SB3086.

| Characteristic | *Bacillus licheniformis* SB3086 | *Bacillus licheniformis* (Type Characteristics)[1,2] | *Bacillus subtilis* (Type Characteristics)[1,2] |
|---|---|---|---|
| Gram Reaction | + | + | + |
| Cell width ($\mu$m) | 0.8 | 0.8 | 0.8 |
| Ellipsoidal spores | + | + | + |
| Motility | + | + | + |
| Anaerobic growth (<1.5 ppm $O_2$) | + | + | − |
| ONPG | + | + | +/− |
| Growth at 55° C. | + | + | − |
| Gelatin Hydrolysis | + | + | + |
| V-P Reaction | + | + | + |
| Nitrate Reduction | + | + | + |

TABLE 1-continued

Comparative Taxonomic Characteristics of *Bacillus licheniformis* SB3086.

| Characteristic | *Bacillus licheniformis* SB3086 | *Bacillus licheniformis* (Type Characteristics)[1,2] | *Bacillus subtilis* (Type Characteristics)[1,2] |
|---|---|---|---|
| Growth in 7% NaCl | + | + | + |
| Starch Hydrolysis | + | + | + |
| Citrate Utilization | − | +/− | + |
| Catalase Positive | + | + | + |
| Casein Decomposition | + | + | + |
| Acid from Glucose | + | + | + |
| Acid from Mannitol | + | + | + |
| Acid from Arabinose | + | + | + |
| Egg-yolk lecithinase | − | − | − |

TABLE 2

Comparative Anti-Disease Activity of SB3086 with other *B. licheniformis* strains.

| *Bacillus licheniformis* Strain | Dollar Spot[1] | Gray Leaf Spot[2] | Rhizoctonia blight[3] | Colletotrichum | Helminthosporium Blight[5] | Pink Snow Mold[4] |
|---|---|---|---|---|---|---|
| SB3086 | 5[6] | 5 | 5 | 5 | 5 | 4 |
| ATCC 25972 | 2 | 1 | 3 | 1 | 3 | 1 |
| ATCC 53757 | 1 | 0 | 1 | 0 | 0 | 1 |
| ATCC 14580 | 1 | 0 | 1 | 1 | 0 | 1 |
| ATCC 11946 | 1 | NA[7] | 1 | 1 | 0 | NA |
| PR1-36a | 1 | NA | 4 | 5 | 5 | NA |

[1]*Sclerotinia homoeocarpa*
[2]*Pyricularia grisea*
[3]*Rhizoctonia solani*
[4]*Microdochium nivale*
[5]*Bipolaris sorokiniana*
[6]Graduated scale with 5 = strong inhibition to 0 = no inhibition
[7]Not assessed

TABLE 3

Fungal inhibition by *B. licheniformis* SB3086 compared with that of other soil bacterial strains

| Culture | Type | *Michrodochium nivale* Trait A | *Michrodochium nivale* Trait B | *Rhizoctonia oryzae* Trait A | *Rhizoctonia oryzae* Trait B | *Sclerotinia homoeocarpa* Trait A | *Sclerotinia homoeocarpa* Trait B |
|---|---|---|---|---|---|---|---|
| SB3086 | *Bacillus licheniformis* | + | + | + | + | + | + |
| SB3002 | *Bacillus amyloliquifaciens* | − | − | − | − | − | − |
| SB3003 | *Bacillus pasteurii* | − | − | − | − | − | − |
| SB3006 | *Bacillus laevolacticus* | + | + | − | + | − | +/− |
| Soy130 | *Bacillus cereus* | − | − | − | +/− | − | − |
| UW8 | *Bacillus sp.* | + | + | + | + | +/− | − |
| 3PMN | *Pseudomonas fluorescens* | − | − | − | − | + | − |
| HC | *Pseudomonas putida* | − | − | − | − | + | − |
| SB3013 | *Enterobacter cloacae* | + | − | +/− | +/− | + | − |
| S1-B | *Pseudomonas sp.* | − | + | NA | NA | − | − |
| BJ-2 | *Pseud. aeureofaciens* | − | + | + | + | − | + |
| G11 | *Bacillus sp.* | + | − | NA | NA | − | − |
| VT-5 | *Bacillus subtilis* | − | − | NA | NA | + | − |
| S1 | *Erwinia sp.* | − | − | − | − | − | − |
| DS1 | *Paenebacillus sp.* | − | − | − | − | − | − |

Trait A
+ = Culture causes mycelia to discolor at interface
− = Culture has no apparent discoloration effect on fungus.
Trait B
+ = Culture causes clear inhibition zone.
− = Culture has no apparent inhibition zone.

TABLE 1-continued

Comparative Taxonomic Characteristics of *Bacillus licheniformis* SB3086.

| Characteristic | *Bacillus licheniformis* SB3086 | *Bacillus licheniformis* (Type Characteristics)[1,2] | *Bacillus subtilis* (Type Characteristics)[1,2] |
|---|---|---|---|

[1]Berkeley, R. C. W., Logan, N. A., Shute, L. A., and Capey, A. G. 1984. In: Methods in Microbiology Vol. 16, Academic Press, London, pp. 291–308.
[2]Bergey's Manual of Systemic Microbiology. 1986. (Sneath, P., Mair, N., Sharpe, M. E., and Holt, J., eds.), Williams and Wilkins, Baltimore, pp. 1123–1131.

TABLE 4

Comparative ability of *B. licheniformis* SB3086 to inhibit the growth of *Aspergillis niger* (common fungi causing darkening of bathroom tile and grout).

| Bacterial Strain | *Aspergillis niger* |
|---|---|
| *Bacillus licheniformis* SB3086 | 5 |
| *Paenibacillus azotofixans* | 0 |
| *Bacillus amyloliquifaciens* | 1 |
| *Bacillus laevolacticus* | 0 |
| *Bacillus cereus* | 4 |

TABLE 5

Field Control of Rhizoctonia blight (Brown Patch) by *B. licheniformis* SB3086

| | | Percent Disease Control (Rhizoctonia blight) | | | |
|---|---|---|---|---|---|
| Location | Plant Type | *Bacillus licheniformis* SB3086 | Daconil ® (chloro-thalonil) | Heritage ® (azoxy-strobin) | Untreated Control |
| Ohio State University | Bentgrass | 78 | 89 | 81 | 0 |
| Clemson University | Fescue | 43 | 81 | 90 | 0 |
| Virginia Polytech. Inst. | Fescue | 58 | 100 | 100 | 0 |

TABLE 6

Components of 710-140 Formulation.

| Ingredient | Amount (w/v) | Range (per L) (w/v) | CAS No. | Purpose |
|---|---|---|---|---|
| *Bacillus licheniformis* SB3086 | 0.14% ($1.1 \times 10^9$ CFU/ml)[1] | 0.001–12% ($1.0 \times 10^6$– $1.0 \times 10^{11}$ CFU/ml) | N/A | Active Ingredient |
| Seaweed Extract Powder | 3.0% | 0.2–10.0% | EPA Manuf. No. 67016-2 | Organic bio-supplement |
| Urea | 25.2% | 1.0–48.0% | 57-13-6 | Nutrient supplement |
| Iron EDTA Chelate, Fe 13% Powder | 1.95% | 0.2–8.0% | 15708-41-5 | Micronutrient supplement |
| Potassium chloride KCl | 0.24% | 0.05–10.0% | 7447-40-7 | Nutrient supplement |
| Disodium dihydro molybdate $Na_2MoO_4 \cdot 2H_2O$ | 0.00024% | 0.00005–0.002% | 10102-40-6 | Micronutrient supplement |
| Cobalt chloride hexahydrate $CoCl_2 \cdot 6H_2O$ | $1.0 \times 10^{-5}\%$ | $1 \times 10^{-7}$– $1 \times 10^{-3}\%$ | 7791-13-1 | Micronutrient supplement |
| Nickel chloride hexahydrate $NiCl_2 \cdot 6H_2O$ | $1.0 \times 10^{-5}\%$ | $1 \times 10^{-7}$– $1 \times 10^{-3}\%$ | 7791-20-0 | Micronutrient supplement |
| Kathon CG/ICP: 5-chloro-2-methyl-4-isosthiazolin-3-one | 5.52 ppm | 0.2–500 ppm | 26172-55-4 | Preservative for shelf concentrate |

[1] Colony Forming Units per ml

What is claimed is:

1. A method for enhancing the fungicidal activity of *Bacillus licheniformis* strain SB3086, comprising providing said strain SB3086 which produces a fungicidal agent that controls growth of fungal organisms or plant disease caused by fungicidal organisms, with a nutrient base that enhances fungicidal activity of said strain SB3086, wherein said nutrient base is 710-140 without *Bacillus licheniformis* strain SB3086.

* * * * *